United States Patent [19]
Prywes

[11] Patent Number: 6,010,518
[45] Date of Patent: Jan. 4, 2000

[54] OPHTHALMOLOGIC INSTRUMENT FOR DISSECTING SCAR TISSUE

[76] Inventor: Arnold S. Prywes, 4212 Hempstead Turnpike, Bethpage, N.Y. 11714

[21] Appl. No.: 09/221,202

[22] Filed: Dec. 23, 1998

[51] Int. Cl.$^7$ ................................................. A61F 9/00
[52] U.S. Cl. ............................................................ 606/162
[58] Field of Search ................................ 604/19, 27, 35, 604/257, 264, 22; 424/427; 128/898; 606/166, 107, 161, 162

[56] References Cited

U.S. PATENT DOCUMENTS

| | | | |
|---|---|---|---|
| 4,300,557 | 11/1981 | Refojo et al. | 604/500 |
| 5,312,330 | 5/1994 | Klopotek | 604/521 |
| 5,699,810 | 12/1997 | Pallikaris | 128/898 |
| 5,800,406 | 9/1998 | Kritzinger et al. | 604/257 |

*Primary Examiner*—George Manuel
*Attorney, Agent, or Firm*—Ladas & Parry

[57] ABSTRACT

An ophthalmologic instrument for dissecting scar tissue from adjacent tissue surfaces in a tissue wall of an eye of a patient, in which the instrument has a rigid housing of a size to enter a space in the eye of a patient and be placed to face a scar to be dissected by the instrument. An inflatable balloon is supported in the housing and in an uninflated state the balloon is substantially confined within the housing and faces an opening at the front of the housing. A pressure source is connected to the balloon for inflating the balloon to cause the balloon to extend from the housing. The front portion of the instrument has a shape to dispose the housing in a position to face the scar and be between the tissue surfaces joined by the scar such that when the balloon is inflated, the scar will be dissected and the tissue surfaces will be separated.

12 Claims, 6 Drawing Sheets

OPHTHALMOLOGIC INSTRUMENT FOR DISSECTING SCAR TISSUE

FIELD OF THE INVENTION

The invention relates to an instrument for dissecting scar tissue from adjacent tissue surfaces at a tissue wall of a patient, and more particularly to tissue surfaces of a failed glaucoma filtering surgery. The instrument is denoted as a needle or cannula balloon plasty device.

The instrument is applicable to the dissection of tissue surfaces in the eye, which have become fused by scarring or membrane formation in the subconjunctival space after a failed glaucoma filtering surgery, in the formation of retinal epiretinal membranes, in the dissection of subretinal neovascular nets, in the treatment of intraocular downgrowth or ingrowth formation, in endoscopic surgery to allow manipulation of other surgical instruments once dissection of scar tissue is complete.

BACKGROUND

Glaucoma is a disease where the intraocular pressure is elevated. It affects significant numbers of our population. The treatment of glaucoma is usually medical. However, medications often fail to control some forms of glaucoma. When further treatment is required a microsurgical operative procedure is performed. This procedure involves constructing a fistula or opening in the tissue wall of the sclera to enhance fluid flow from the internal portion of the eye (ciliary body) which secretes the fluid (aqueous humor) through the newly formed opening. This opening does not remain open in some patients due to the formation of scar tissue which seals down the fistula. This scarring is a difficult problem in post surgical glaucoma filtering surgery. Filtering surgery failure or loss of effectiveness has required intervention in many cases. The existing technology for treatment of failed filtering blebs (subconjunctival fluid-filled chamber) includes the use of a fine needle to incise the scar tissue and to manipulate the scar tissue at the fistula site. The use of such a fine needle (25–30 gauge) to dissect the scarred down subconjunctival space and to inject antimetabolites has a significant risk of buttonholing or penetrating vital tissues. This can result in wound leaks, infections or increased bleeding.

SUMMARY OF THE INVENTION

It is an object of the invention to provide an ophthalmologic instrument for dissecting scar tissue between adjacent tissue surfaces at a tissue wall of the eye of a patient which will minimize the problems associated with the existing technology as described above.

A particular object of the invention, is to provide such an instrument which will be in the form of a needle or cannula which is adapted for being located in a suitable position to effect dissection of the scar tissue by inflation of a balloon.

A feature of the invention is to use a balloon to dissect the scar tissue instead of a fine needle.

According to the invention, an ophthalmologic instrument is provided which comprises a rigid housing of a size to enter a space in the eye of a patient and be placed adjacent to a scar to be dissected by the instrument, said housing supporting an inflatable balloon therein and having a front portion with an opening through which the balloon extends when inflated, said front portion of the instrument having a shape to dispose the housing in a position to face the scar between tissue surfaces joined by said scar, such that when the balloon is inflated said scar will be dissected and said tissue surfaces will be separated.

In further accordance with the invention, the housing is tubular and has a longitudinal axis, the front portion of the housing having a planar leading edge extending at an acute angle relative to the longitudinal axis of the housing. In the uninflated state, the balloon is confined within the housing.

In further accordance with the invention, the leading edge of the housing forms a sharp cutting edge at said front portion for initially dissecting the scar before the balloon is inflated.

In further accordance with the invention, an open end of the balloon is secured to a removable cap at the distal or back end of the housing and a fluid pressure source is connected by a conduit to the open end of the balloon via said cap for selectively inflating the balloon.

In further accordance with the invention, the sharp cutting edge at the front portion of the housing, is so located to effect the initial dissection of the scar while the front portion of the housing supports and elevates one of the tissue surfaces in preparation for inflation of the balloon.

BRIEF DESCRIPTION OF THE FIGURES OF THE DRAWING

FIG. 7a is a sectional view taken on line 7a—7a in FIG. 6a.

DETAILED DESCRIPTION OF PREFERRED EMBODIMENTS OF THE INVENTION

The invention will be described hereafter with reference to embodiments thereof for dissecting scar tissue formed in the subconjunctival space in the eye of a patient following a failed filtering surgery. The invention is also applicable to a number of other procedures in which a scar is to be dissected to separate the surfaces at a tissue wall.

Figure 1:
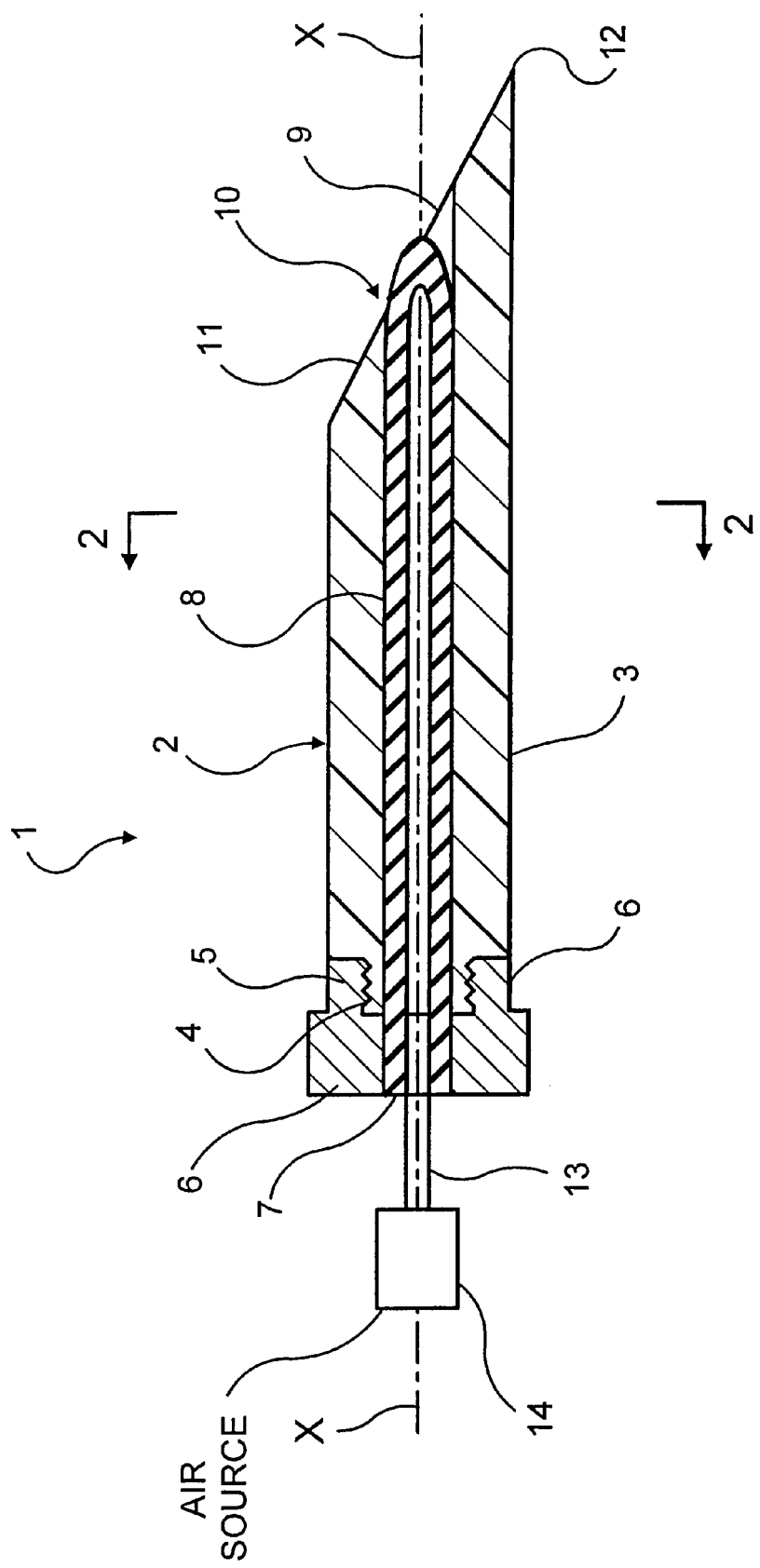
FIG. 1 is a longitudinal cross-sectional view through one embodiment of the instrument according to the invention.

Referring to FIG. 1, therein is seen an instrument 1 in the form of a cannula or needle 2 which comprises a housing 3 of rigid material which is longitudinally elongated along a longitudinal axis X—X. The housing 3 is made of a plastic material but it can also be made of any other rigid material, such as metal, ceramic, etc. At its rear or distal end portion 4, the housing 3 is provided with a threaded connection 5 for removably joining a cap 6 therewith. Secured to the cap 6, is an open end 7 of an inflatable balloon 8 shown in FIG. 1 in an uninflated state. The balloon 8 extends from the cap 6 into a channel 9 in the housing. The balloon is substantially confined in the channel 9 and the closed front end of the balloon is located at the forward or proximal end 10 of the housing.

Figure 2:
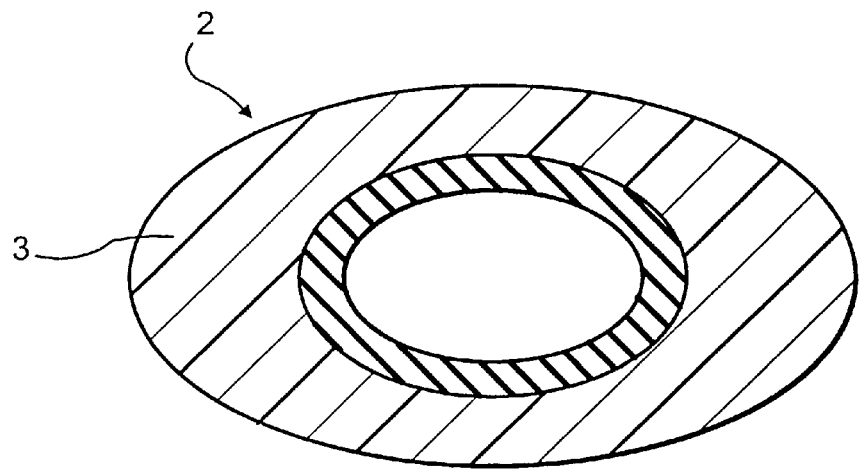
FIG. 2 is a cross-sectional view taken along line 2—2 in FIG. 1.

As seen in FIG. 2, the housing 3 is of tubular shape and specifically, is of elliptical shape. The housing 3 can also have a circular cross-sectional shape. In the embodiment of FIG. 2, the balloon has a width that is greater than its height to provide a flattened configuration so that when the balloon is inflated and extended from the housing, it will incise the scar along the greater width dimension of the balloon as will become evident later.

The dimensions of the housing are such to enable the housing to enter a space in the eye of a patient and be placed to face a scar to be dissected by the instrument. In this respect, the housing has a maximum width, along the major axis of the elliptical cross-section which is 3 mm or less and preferably 2 mm or less and a maximum width along the minor axis of the elliptical cross-section of about 1.5 to 2 mm. The housing has an axial length of about 2 cm.

At its forward or proximal end 10, the housing has a front or leading edge 11 which lies in a plane disposed at an acute angle with respect to the longitudinal axis X—X to form a sharp tip or edge 12 at the lower generatrix surface of the housing 3. The angle of the leading edge 11 with respect to the longitudinal axis X—X of the housing is illustrated in FIG. 1 as about 25° but this angle can vary depending on particular conditions of the patient and the scar to be dissected. At the distal end of the housing, the open end 7 of the balloon is sealingly connected to a conduit 13 attached to a fluid pressure source 14, for example, compressed air or saline solution.

Figure 3:
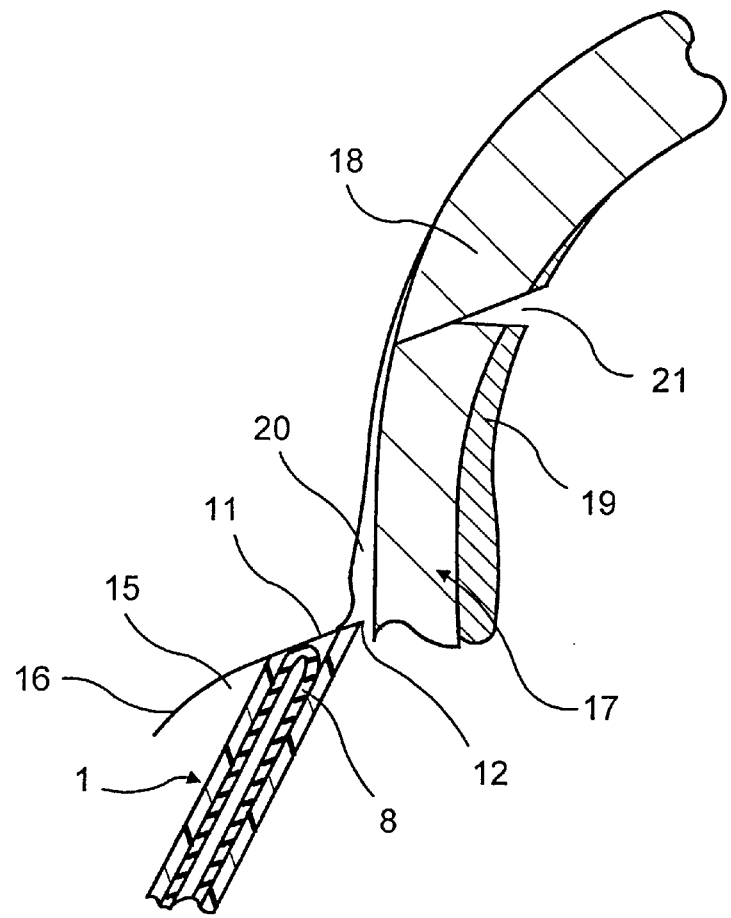
FIG. 3 is a diagrammatic view showing the instrument in FIG. 1 in a first stage of operation to dissect a scar formed after filtering surgery.

FIG. 3 diagrammatically illustrates a first stage of operation of the instrument 1. In this stage, the instrument has been inserted through an incision (not shown) formed in the eye structure to enter the subconjunctival space 15 located between the conjunctiva 16 and a tissue wall 17 formed by the sclera 18 and the trabecular meshwork 19. Prior to insertion of the instrument into the subconjunctival space 15 an injection of an anesthetic and/or an antimetabolite can be effected. Instead of normally being substantially free from the sclera 18, the conjunctiva 16 is joined to the sclera by a scar 20 due to a prior failed filtering surgery. The scar 20 is formed at a previous filtering bleb site. Because of the scar 20, a previously formed fistula 21 at the juncture of the trabecular meshwork 19 and the sclera 18 becomes disrupted and no longer allows escape of aqueous humor from the anterior chamber to the subconjunctival space to act as a drain to reduce the intraocular pressure within the eye.

In the stage shown in FIG. 3, the sharp tip or edge 12 of the instrument has pierced the conjunctiva to form the incision through which the instrument has entered the non-scarred region of the subconjunctival space 15. The sharp tip or edge 12 of the instrument is then utilized to initially incise the scar 20 while the leading edge 11 of the housing 3 supports and elevates the subconjunctiva 16 from the scar 20.

Figure 5:
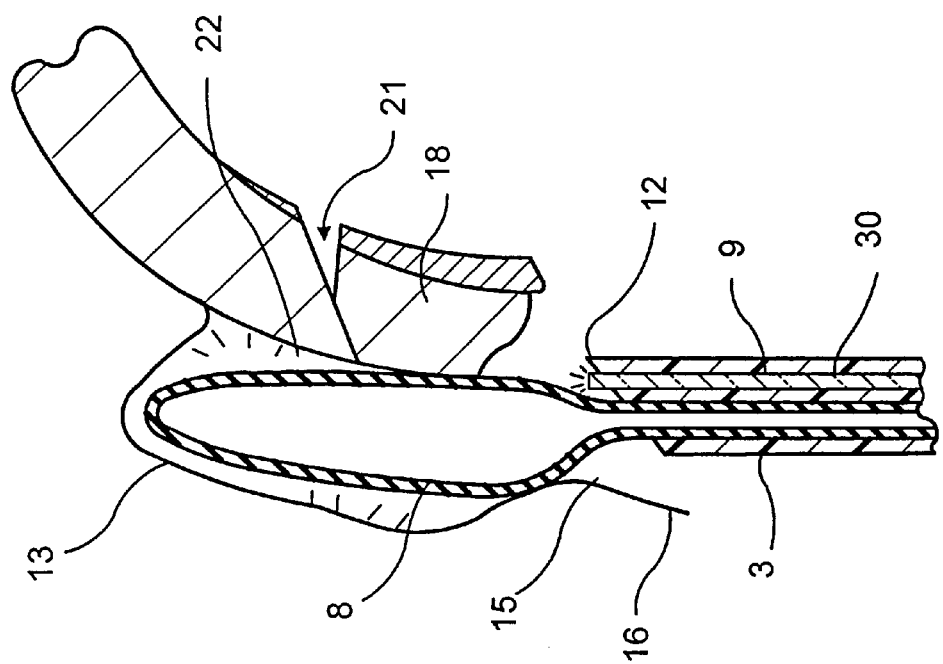
FIG. 5 shows the instrument of FIG. 4 in a completed stage of the operation.
Figure 4:
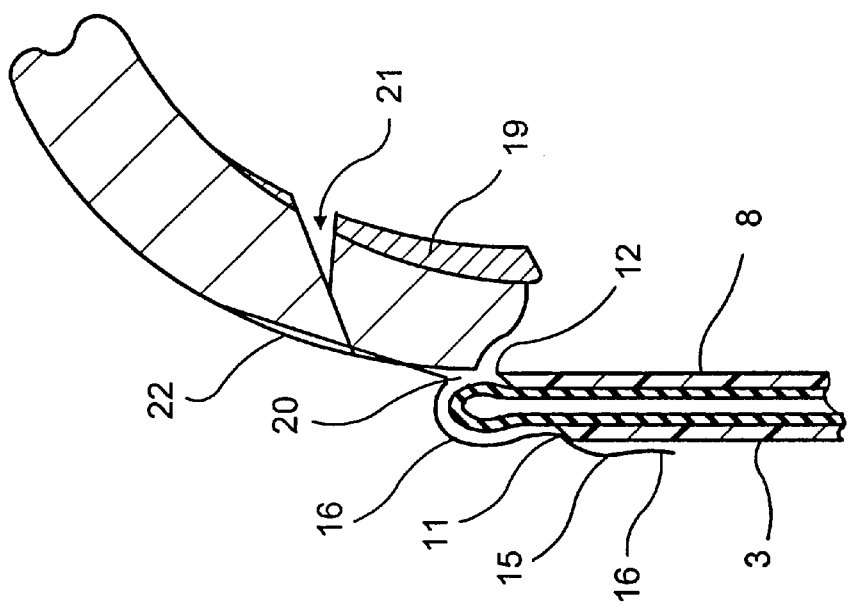
FIG. 4 shows the instrument in FIG. 3 in a further stage of operation.

The balloon 8 is thereafter inflated and FIG. 4 shows the partially inflated state of the balloon within the subconjunctival space 15. The tissue of scar 20 which was initially dissected by the sharp tip or edge 12, is now progressively dissected further as the balloon is inflated, and as seen in FIG. 5, during its inflation the balloon elevates the conjunctiva 16 to achieve the dissection of the scar. A remaining portion of the scar is shown at 22, above the fistula 21.

In the stage of inflation shown in FIG. 5, the conjunctiva 16 has been separated from the sclera to enlarge the subconjunctival space 15 at the fistula 21. Effectively, the scar 20 has been dissected to provide the separation of the subconjunctiva 16 from the sclera 18 to allow free outflow of fluid through the fistula. The fistula will now function to relieve the intraocular pressure. The balloon is now deflated and the instrument is removed from the eye.

After the incision of the scar tissue by the tip 12 and the partial inflation of the balloon as shown in FIG. 4, the cannula is retracted as the balloon is inflated further in order to prevent contact of the tip 12 and the inflated balloon.

Figure 6:
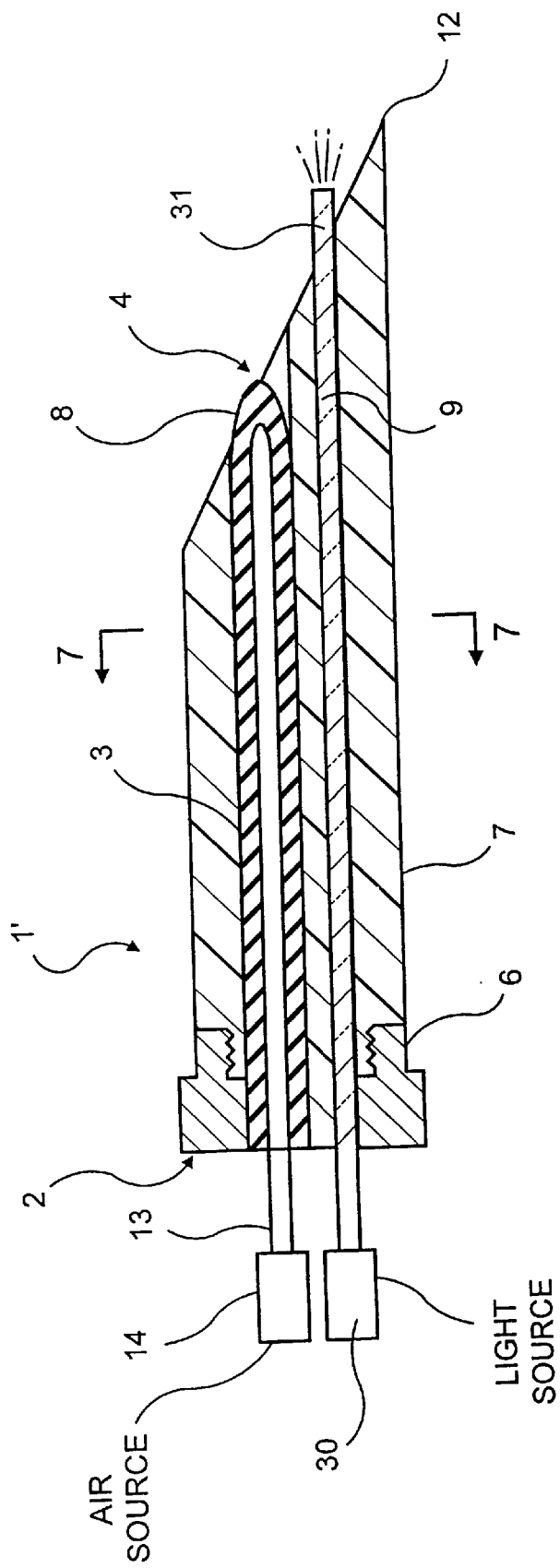
FIG. 6 is a longitudinal sectional view of a modified embodiment of the instrument of FIG. 1.
Figure 7:
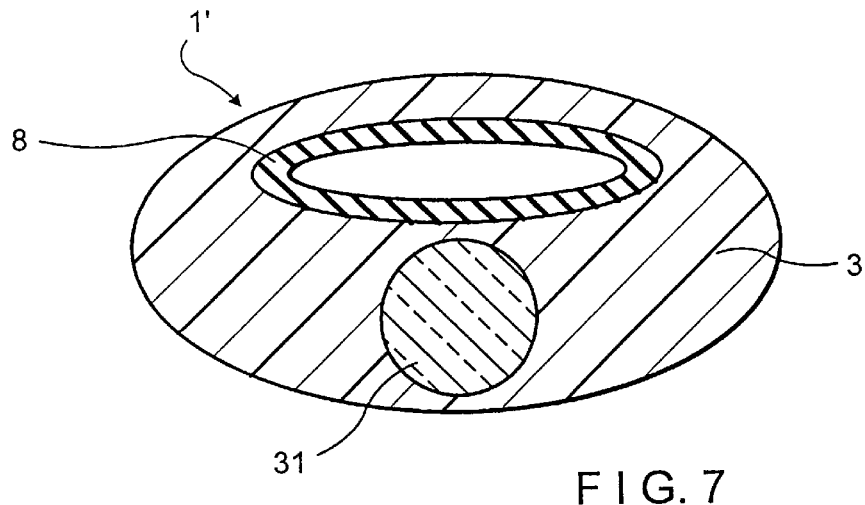
FIG. 7 is a sectional view taken on line 7—7 in FIG. 6.

FIG. 6 shows another embodiment of the instrument which is similar to the embodiment of FIG. 1 and employs a number of the same elements which are designated by the same reference numerals. In FIG. 6, a light source 30 is connected to an optical fiber 31 supported within the housing 3 at a location below the balloon 8 and in transverse alignment therewith as shown in FIG. 7. The optical fiber 31 serves to transmit a light beam to the site at which the scar is being incised.

Figure 6A:
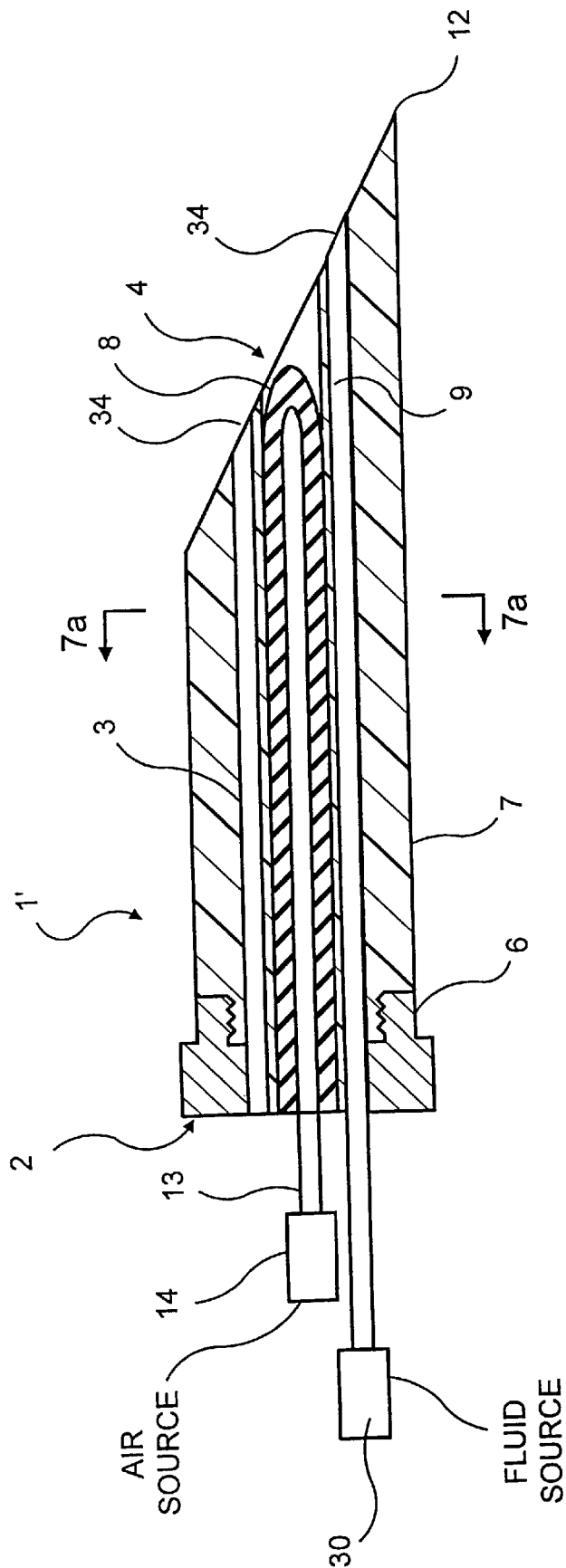
FIG. 6a is a longitudinal sectional view of another modified embodiment of the instrument of FIG. 1.
Figure 7A:
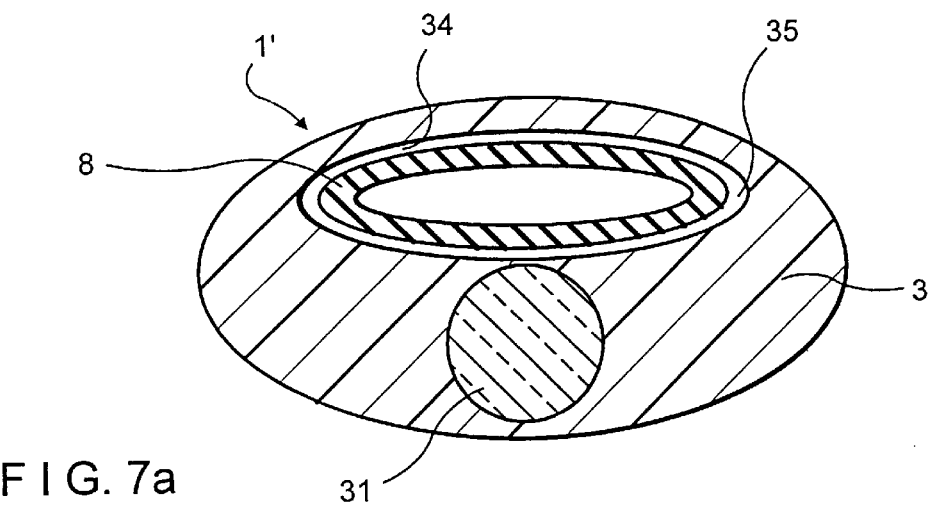

FIGS. 6a and 7a illustrate another embodiment of the instrument which is similar to the embodiment of FIG. 1 and employs a number of the same elements which are designated by the same reference numerals. In the embodiment of FIGS. 6a and 7a, a fluid injections means 33 is provided which supplies fluid into a space 34 defined between the rigid inner surface of the wall of the cannula and the outer wall of the deflated balloon 8. The space 34 serves to deliver fluid, such as anesthetic, air, antimetabolite or other fluid into the subconjunctival space 15 to treat the patient or allow further advancement of the cannula prior to balloon dissection.

Figure 8:
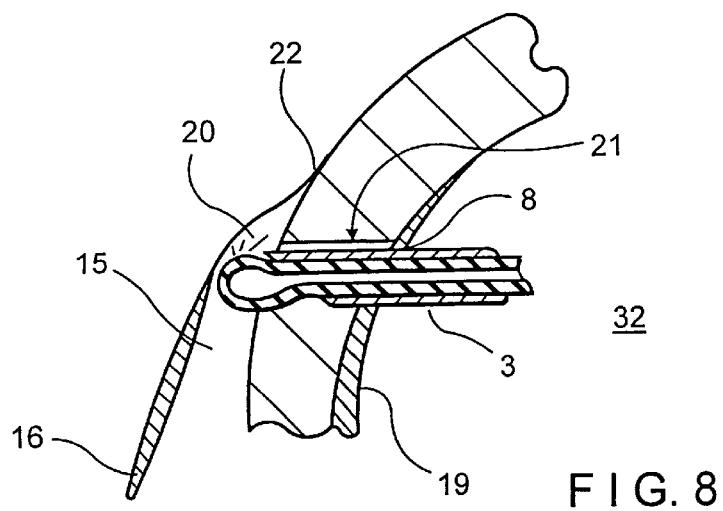
FIG. 8 is a view similar to FIG. 3 showing the use of the instrument in an ab-intemo procedure.

In FIGS. 3–5 the instrument has been illustrated in an ab-extemo procedure in which the instrument is introduced through the conjunctival space 15. As shown in FIG. 8, the instrument can also be used in an ab-intemo procedure in which the instrument is introduced through the anterior chamber 32 of the eye. In this case, the sharp tip or edge 12 is engaged at the posterior surface of the sclera and the balloon is inflated to extend through the fistula 21 to move the conjunctiva away from the sclera and dissect the scar tissue 20.

Although the invention has been described in relation to specific embodiments thereof, it will become apparent to those skilled in the art that numerous modifications and variations can be made within the scope and spirit of the invention as defined in the attached claims.

What is claimed is:

1. An ophthalmologic instrument for dissecting scar tissue from adjacent tissue surfaces in an eye of a patient, said instrument comprising:

a housing of a size to enter a space in the eye of a patient and be placed to face a scar to be dissected by the instrument, an inflatable balloon supported in said housing, said housing including a front portion having an opening, said balloon having an uninflated state in which the balloon is substantially confined within said housing and faces said opening, and means for inflating said balloon to cause the balloon to extend from said housing via said opening, said front portion of said instrument having a shape to dispose said housing in a position to face said scar between tissue surfaces joined by said scar such that when the balloon is inflated, said scar will be dissected and said tissue surfaces will be separated.

2. An ophthalmologic instrument as claimed in claim 1, wherein said housing is tubular and has a longitudinal axis, said front portion of the housing having a planar leading edge extending at an acute angle relative to said axis of said housing.

3. An ophthalmologic instrument as claimed in claim 2, wherein said leading edge forms a sharp tip at said first portion of the housing serving as a cutting edge for initially dissecting the scar before inflating the balloon.

4. An ophthalmologic instrument as claimed in claim 3, comprising means for producing a light beam from said housing to illuminate the scar.

5. An ophthalmologic instrument as claimed in claim 3, wherein said housing is provided with a longitudinally extending channel in which said balloon is disposed.

6. An ophthalmologic instrument as claimed in claim 5, wherein said housing includes a removably secured end cap, said balloon having an open end secured in said end cap and a remaining portion with a closed end in said channel when the balloon is deflated, said means for inflating said balloon including a fluid pressure source, and a conduit connecting said fluid pressure source and said open end of the balloon.

7. An ophthalmologic instrument as claimed in claim 3, wherein said sharp tip is disposed proximally at said front portion at a position of the sized housing to effect the initial dissection of the scar while said front portion supports and elevates one of the tissue surfaces in preparation for inflation of said balloon.

8. An ophthalmologic instrument as claimed in claim 7, wherein the tissue surfaces are formed on the conjunctiva and the scleral wall which are joined by said scar at a fistula in the scleral wall, said instrument and said balloon being dimensioned so that said sharp tip initially incises said scar and said balloon dissects the scar to separate the conjunctiva from the scleral wall at said fistula.

9. An ophthalmologic instrument as claimed in claim 1, wherein said housing has a longitudinal channel in which said balloon is supported, said channel having a width in transverse cross-section which is greater than its height so that the balloon has a flattened configuration in transverse section.

10. An ophthalmologic instrument as claimed in claim 1, wherein said housing is made from a rigid material.

11. An ophthalmologic instrument as claimed in claim 1, comprising means for conveying fluid through said housing to said opening at said front portion of the housing.

12. An ophthalmologic instrument as claimed in claim 11, wherein said means for conveying fluid comprises a fluid injection means connected to said housing to introduce fluid into a space between an outer surface of said balloon and an inner surface of the housing surrounding said balloon.

* * * * *